(12) United States Patent
Harder et al.

(10) Patent No.: US 6,792,066 B1
(45) Date of Patent: Sep. 14, 2004

(54) METHOD AND CONTROL DEVICE FOR CONTROLLING A TOMOGRAM ACQUISITION DEVICE

(75) Inventors: Martin Harder, Nuremberg (DE); Niels Oesingmann, Buckenhof (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 10/438,546

(22) Filed: May 15, 2003

(30) Foreign Application Priority Data

May 15, 2002 (DE) .......................................... 102 21 642

(51) Int. Cl.[7] .............................................. A61B 6/03
(52) U.S. Cl. ................................ 378/4; 378/8; 378/15; 378/901
(58) Field of Search .......................... 378/4, 8, 15, 19, 378/901; 250/363.04, 370.09

(56) References Cited

U.S. PATENT DOCUMENTS

| | | | |
|---|---|---|---|
| 5,431,161 A | * 7/1995 | Ryals et al. | ................. 600/425 |
| 5,719,498 A | 2/1998 | Hausmann | |
| 5,722,405 A | * 3/1998 | Goldberg | .................... 600/407 |
| 5,803,914 A | * 9/1998 | Ryals et al. | ................. 600/407 |
| 6,381,487 B1 | * 4/2002 | Flohr et al. | ................. 600/425 |

FOREIGN PATENT DOCUMENTS

| | | |
|---|---|---|
| DE | 100 48 438 A1 | 4/2000 |
| DE | 198 46 687 C2 | 7/2001 |

OTHER PUBLICATIONS

"ECG_Triggered Snapshot MR Imaging of the Heart," Liu et al., Computers in Cardiology, 1990 Proceedings, Sep. 23–26, 1990, pp. 381–384.

* cited by examiner

Primary Examiner—David V Bruce
(74) Attorney, Agent, or Firm—Schiff Hardin LLP

(57) ABSTRACT

In a method for controlling a tomogram acquisition device acquiring tomograms of a subject and a control device and tomography apparatus operating according to the method, reference images of the subject are presented at a graphic user interface, and the positions of tomograms to be subsequently acquired are defined by slice position markings within the displayed reference images. A sequence of time-dependent slice position markings is first set in the reference images, with a time mark being allocated to the individual slice position marking of the sequence. On the basis of this sequence of time-dependent slice position markings, the positions of the tomograms to be subsequently acquired are determined dependent on the acquisition time of each tomogram relative to a reference time.

25 Claims, 5 Drawing Sheets

METHOD AND CONTROL DEVICE FOR CONTROLLING A TOMOGRAM ACQUISITION DEVICE

BACKGROUND OF THE INVENTION

1. Field of the Invention

The present invention is directed to a method for controlling a tomogram acquisition device for acquiring tomograms of an examination subject, of the type wherein reference images of the subject are presented by means of a graphic user interface, and the positions of tomograms to be subsequently acquired are defined by slice position markings entered within the displayed reference images. The invention also is directed to a corresponding control device for a tomogram acquisition device as well as to a tomogram acquisition device having such a control device.

2. Description of the Prior Art

Tomograrn acquisition devices such as, for example, X-ray computed tomography systems and nuclear magnetic resonance tomography systems are primarily employed in the medical field. In most instances, the tomogram exposures serve the purpose of examining body parts or organs of a patient for a later diagnosis. They also are often employed in the context of surgical interventions. For example, German PS 198 46 687 discloses a method wherein a relatively exact three-dimensional presentation of the operation region is first recorded pre-operatively by means of a magnetic resonance apparatus. Moreover, ultrasound image data of the operation region are acquired with an ultrasound head both pre-operatively and at various points in time during the operation. Changes of the region being operated on are determined by comparing the ultrasound image data acquired at the various points in time, and the three-dimensional magnetic resonance dataset is updated on the basis of these changes and displayed. If a magnetic resonance imaging method that that produces an image of sufficient detail cannot be intra-operatively employed, this method makes it possible to generate "artificial magnetic resonance images" with the assistance of a relatively simple ultrasound acquisition method.

Further, a large variety of tomogram acquisition methods can be employed for the non-destructive examination of arbitrary, other subjects.

When using such tomogram acquisition methods, it is fundamentally desirable for optimally few exposures of the person or article under examination to be acquired so that an unambiguous, dependable examination result is achieved. This is especially important in the medical field since the examination time, what is usually uncomfortable for the patient, and possibly the radiation stress as well, can be reduced in this way. To this end, it is necessary that the positions of the tomograms to be acquired be selected such that the object of the examination within the article or person, for example a specific organ of a patient, is covered in a suitable way in the tomograms.

Particularly when examining a patient, however, the region of interest cannot always be exactly localized in advance from the outside since, first, the exact position of an organ in the body of the patient is dependent on the individual anatomy of the patient and, second, the region of the organ under examination wherein a pathological change that must be examined in greater detail is situated becomes clear only during the course of the examination.

In order to exactly position tomograms, the initially cited control method is currently generally employed. For example, standard tomograms of the test subject or of the body part to be examined, for example the head or the chest area, are first generated as reference images. The acquisition of the reference images usually ensues within the tomogram acquisition device itself. It is also possible, however, to employ tomograms generated with some other device insofar as there is a possibility of suitably positioning the patient under examination in the tomogram acquisition device on the basis of the exterior anatomy. With the assistance of suitable input means, for with a standard computer mouse, a graphics tablet, a keyboard or the like, the operator of the tomogram acquisition device can then set slice position markings within the reference images, for example in the form of section lines and/or projection presentations. In the medical field, a sagittal image, a coronary image and a transverse image are often generated as the reference images. In order to generate a simple plane within the three-dimensional examination subject, a slice position marking in the form of a section line in two of the images and a further slice position marking in the form of a projection presentation in the third image are usually required. Moreover, it is possible to set the size or the thickness of the slices. Usually, a number of slices to be acquired can be immediately marked within the reference images, for example a group of a number of parallel slices, in order to thus cover the region of the structure to be examined in the best way. This method of defining the positions of the tomograms to be acquired by means of a marking in reference images of the subject, which is rather comfortable for the user, is called "graphic slice positioning" (GSP). Further parameters required for the control of the tomogram acquisition device also can be defined for the individual tomograms to be acquired. In a magnetic resonance tomography apparatus, for example, these are the relaxation time TA and the echo time TE, etc., or for an X-ray computer tomography system, the dose to be set, etc. When the operator has set all parameters and optimally covered the measurement region with the planned slices, the measurement can be started by means of what is referred to as a "measurement queue". The data of the slice position markings within the reference images are then converted into position data within the examination subject, and the tomogram acquisition device, or the scanner is driven such that the desired images are generated at the corresponding slice positions within the examination subject. The generated tomograms are then stored in an image databank. All measured images are directly available for further slice positioning, i.e. they can in turn be employed as reference images at the user interface in order to enter new slice position markings for further measurements.

Various methods of generating tomograms with the assistance of a graphic slice positioning are described, for example, in German OS 100 48 438 and 195 29 636.

German OS 100 48 438 discloses a method that generates a rotated presentation of the reference image dependent on a command input by a user and generates a spatial presentation of the slices on the picture screen corresponding to the rotation of the reference image. As a result, the spatial orientation of the slices that have been selected and are to be measured is visualized for the user with respect to the reference image of the measured body part of the patient. Particularly in instances of doubly inclined slice groups, the user can understand the actual situation in a simple way and judge whether the planned slices that are presented in the reference images in fact cover the region or the body part to be examined, without the user having to be exceptionally capable of imaging spatial relationships.

German OS 195 29 636 likewise discloses producing an overview exposure of the subject perpendicular to the desired slices and then graphically positioning the desired slices on the basis of the overview exposure. A 3D dataset that covers the prescribed slices is to be subsequently produced. The desired slices are then reconstructed from the 3D dataset and ultimately imaged.

A problem of all of the aforementioned methods occurs when the orientation of the subject changes perpendicularly to the desired image plane over time. In this case, the structures of interest are no longer completely imaged. The image plane therefore must be readjusted in conformity with the motion. A typical example of this is the examination of a heart valve of a patient. The position of the heart valve changes constantly due to respiration and the heart activity. A simultaneous derivation of motion information from the subject of interest for image readjustment is generally not possible in two-dimensional imaging because the structure to be examined, for example a heart valve, is often too small and relatively poorly delimited. Moreover, the motion measurement and the image measurement must be implemented temporally separated, with the motion measurement to be prospectively implemented influencing the image signal. In practice, indirect methods therefore are currently employed that determine the motion component of interest for the structure to be actually examined from the motion of a different structure, for example of a different organ of the patient. A method that is often utilized is referred to as "navigator echo technique", wherein the signal from the tomogram acquisition device, and thus the position of a reference structure is acquired, for example, a linear coupling is determined between the current orientation of the reference structure and the structure to be examined. For example, the position of the diaphragm is identified with this method in order to correct the respiratory position of the heart. A disadvantage of this method is that not only the structure to be examined but also the reference structure must be permanently measured in order to determine the dislocation. A part of the measuring time thus no longer is available for measuring the structure that is actually wanted. This problem exists in all methods that make use of a reference structure for the readjustment of the measurement slice.

A method referred to as the "slice tracking method" also is known, wherein the motion of a structure as a function of time is measured in advance and the motion of the measured slice is calculated therefrom in advance. This method has the disadvantage that it can be applied only for certain structures that are large enough for such an examination such as, for example, the diaphragm or the liver of a patient. It cannot be applied in the case of smaller structures such as, for example, heart valves. In such cases, an indirect method must be used wherein the motion of the valve is derived, for example, from the upper myocardium of the heart.

SUMMARY OF THE INVENTION

An object of the present invention is to provide an alternative control method for tomogram acquisition devices and a corresponding control device, which allow a simple, time-dependent slice positioning that can be universally applied for various examinations and that, in particular, allow a reliable readjustment of the position of the tomograms, so that small structures under examination can be reliably observed over a longer time span.

This object is achieved in a method according to the invention wherein a sequence of time-dependent slice position markings, i.e. at least two slice position markings, is first set in the reference images, and a time mark is allocated to the individual slice position markings. The time mark can refer to a specific reference point in time or to the time markings of the other slice position markings of the sequence, i.e., for example, relative time intervals are allocated to the individual slice position markings. Using this sequence of time-dependent slice position markings, the positions of the tomograms to be subsequently acquired are determined dependent on the acquisition time of the respective tomogram relative to a reference time, for example relative to a starting point of the measurement or relative to the acquisition time of the previous tomogram.

Due to the possibility of linking the respective slice position markings with a time mark, the operator can interactively specify the position of each image plane, and thus an arbitrary path of a series of exposures within the subject as a function of the time. The operator also can exactly plan a measurement series relative to the time component and thus optimally adapt it to the particular examination. The motion of the structures of interest also can be taken into consideration, so that additional, complicated measurements for the readjustment of the image plane are not necessary.

As used herein "position" and positioning mean not only the definition of the spatial location of the slice but also its orientation, as well as - in some circumstances—the shape and the volume of the slice a specific locations, i.e. the position of each volume element. The slices may be planar, plane-parallel slices or may be hyperbolic planes. For simplicity but not as a limitation, the following discussion is based on the positioning of a planar tomogram.

A control device for the implementation of the method employs a standard user interface with a graphic user interface for the presentation of the reference images and with means for setting slice position markings. Moreover, a slice position determination unit is required for determining the position of tomograms of the subject to be subsequently acquired on the basis of the slice position markings in the reference images. For example, the determination of the positions in the subject from the slice position markings can ensue by means of a simple conversion of the graphics data into the positions coordinates in the test subject. Further, an operating unit is required in order to drive the tomogram acquisition device such that tomograms of the subject are recorded at the positions determined by the slice position determination element. For example, the operating unit includes interfaces, D/A converters, etc., for driving the various components of the tomogram acquisition device such as motor actuators or electromagnets, transmission/reception coils for the magnetic resonance signal, etc. Inventively, the control device also includes a setting unit to set a sequence of time-dependent slice position markings in the reference images and to allocate respective time marks to the individual slice position markings of the sequence. The slice position determination unit operates such that, on the basis of the sequence of time-dependent slice position markings, it determines the positions of tomograms to be successively acquired dependent on an acquisition time of the respective tomogram relative to a reference time.

A series of tomograms to be acquired at various points in time can be determined in a single reference image, or in two or three reference images that show the subject from various points of view at a specific point in time. In a preferred exemplary embodiment, however, a sequence of time-dependent reference images is generated first that show the subject at different relative points in time relative to a reference time, or at defined time intervals relative to one another. On the basis of the time-dependent reference images, the operator is able to acquire information about how a specific tomogram should be optimally positioned at a specific relative point in time and can accordingly set the slice position marking.

It is preferred to set a slice position marking in a time-dependent reference image that is automatically allocated to the relative point in time of the reference image itself, as the time mark. Preferably, exactly one slice position marking is set in each of the time-dependent reference images. The control device includes an allocation unit for this purpose that allocates the relative points in time of the respective reference image to the slice position markings as the time mark.

Preferably, the sequence of time-dependent reference images is generated during an event that corresponds to the event during the later measurement of the tomograms for the examination. This can be periodically reoccurring events such as, for example, the respiratory or heart motion of the patient, or singly triggered events such as, for example, a swallowing motion. For example, the patient can first swallow a contrast agent for examining the esophagus during a swallowing motion. A sequence of reference images is acquired during this first swallowing event. The operator of the tomogram acquisition device then sets the slice position markings in these reference images in order to define the relative points in time and the relative region of the esophagus in which a tomogram is to be generated. Subsequently, the actual examination is implemented during a repetition of the swallowing event.

The sequence of time-dependent reference images preferably shows a specific, moving structure of the subject to be acquired such as, for example a heart valve in different positions, i.e. at least one component of the motion direction of the structure of interest should lie in the image plane of the time-dependent reference images. The slice position marking is then set in each of the time-dependent reference images such that a slice of the subject that encompasses this structure of the subject is marked. In an examination of a heart valve, this means the slice position marking is set such that the marked slice includes the heart valve in each of the time-dependent reference images.

In the simplest case, the tomograms are respectively acquired at points in time in the following measurement series that each correspond exactly to a time mark of a slice position marking. The tomogram is then acquired exactly at the position corresponding to the slice position marking.

Preferably, however, a time-dependent positioning function and/or a reference table is generated from the sequence of time-dependent slice position markings. The positions of the tomograms at arbitrary relative acquisition times then can be determined on the basis of this time-dependent positioning function or the reference table (look-up table). The data of the sequence of time-dependent slice position markings can form the supporting points of the function or the entries of the look-up table, or they can form supporting points for generating a more complex look-up table. The positioning function can be implemented with standard mathematical methods, for example with arbitrary, suitable fit and interpolation methods with which functions are generated on the basis of supporting points. This can ensue segment-by-segment with respect to the time. Likewise, the look-up table can be completed using suitable interpolation methods when being generated between the individual supporting points. Given employment of a look-up table, known interpolation methods can be accessed for determining positions for acquisition times that lie between the entries of the look-up table.

The relative points in time of the individual tomograms of the later measurement series can be selected independently of the temporal position of the reference images that are employed. As a result, it is possible to generate only a small number of reference images with large temporal spacings for the inventive graphic slice positioning and to subsequently acquire a series of tomograms that is relatively dense in terms of time in the actual examination. The overall examination duration can be shortened, and the number of reference images can be reduced to a minimum, particularly in an examination with an X-ray computed tomography apparatus, and thus the radiation exposition time of the patient can be shortened.

The control device preferably is able to implement an exposure series, with the starting point of the exposure series serving as the reference time for determining the positions of the individual tomograms dependent on the respective acquisition time.

The occurrence time of a specific event occurring in or at the subject can be selected as the starting time. Such an event can be, for example, the aforementioned initiation of a swallowing event or, in the case of a heart examination, a specific event within the heart motion, for example the occurrence of the typical r-wave or s-wave in the EKG of the patient being examined. A triggering of a simple MR exposure by the r-wave of an EKG is described, for example, in the article "ECG-Triggered Snapshot MR Imaging of the Heart", Computers in Cardiology, Proceedings 23–26 September 1990, pp. 381–384, by Y. Liu, S. J. Riederer, D. G. Brown, R. C. Wright, A. E. Holsinger, R. C. Grimm and R. L. Ehman.

To this end, the control device preferably includes an arrangement for determining the event at or in the subject as the reference time, for example a suitable measuring instrument. Alternatively, a signal of an external measuring instrument that is connected to the control device via an interface can be employed. The measuring instrument can automatically generate a trigger signal given occurrence of the event that triggers the start of the exposure series.

The exposure series can be periodically repeated. In an examination at the heart, for example, several image series can be acquired that are each implemented within an r-r interval measured in an EKG, whereby triggering can also ensue at a new r-blip each time. It is not necessary that the tomograms always be implemented at the same relative points in time with respect to the reference time; rather, tomogram exposures can be generated at individual points in time in each image series, with the position of each tomogram being re-determined dependent on the relative acquisition time.

The inventive control device can be largely realized in the form of suitable software on a computer having an adequate computing power. This can be a standard computer with appropriately adapted interfaces for controlling the tomogram acquisition device.

In particular, the slice position determination unit that defines the exact positions of the tomograms within the subject on the basis of the slice position markings in the reference images and calculates the positions dependent on the relative acquisition time can be installed on a processor of the computer in the form of software modules.

Likewise, the components of the user interface that edit the image data for presentation on the graphic user interface and that convert the commands of a mouse, a keyboard or similar input devices into data in order to set the markings on the graphic user interface, can be realized on this processor, or on a separate computer that has the user interface as a terminal.

Further, the devices for the automatic control of the tomogram acquisition device for acquiring a series of reference images or the later, actual series of examination images, the unit for registering the information about the relative point in time of the reference images, the allocation unit which allocates the relative point in time of a reference image to a slice position marking as time mark, as well as the unit for determining a positioning function and/or a reference table from the reference data can be realized in the form of software modules.

A modification of an existing control device of conventional tomogram acquisition device is therefore possible in a relatively simple way to program it to operate according to the inventive method.

DESCRIPTION OF THE PREFERRED EMBODIMENTS

Figure 1:
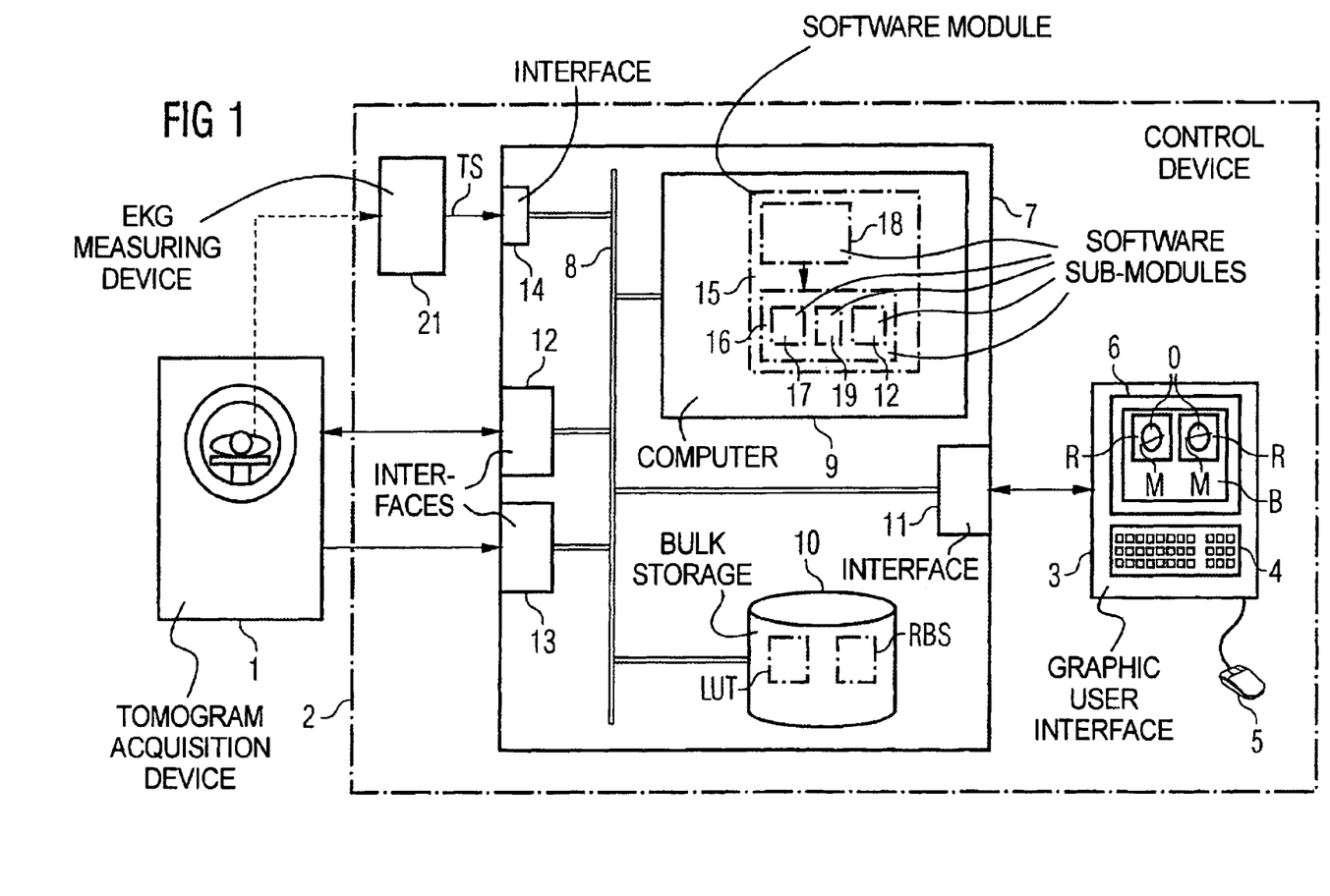
FIG. 1 is a schematic illustration of a tomogram acquisition device with an inventive control device.

The tomogram acquisition device 1 shown in FIG. 1 is a magnetic resonance tomography apparatus 1 in which a patient under examination is situated on a patient bed.

This magnetic resonance tomography apparatus 1 is controlled by a control device 2. The control device 2 is thereby essentially composed of a mainframe 7 and a terminal 3 that is connected to the computer 7. An operator can operate the control device 2 and thus, the magnetic resonance tomography apparatus 1 via the terminal. To this end, the terminal 3 has a user interface that is composed of a standard picture screen 6 with a graphic user interface B displayed thereon, a keyboard 4 and a mouse 5.

The magnetic resonance tomography apparatus 1 is connected to the control device 2 via interfaces 12 and 13 here. Usually there are multiple individual interfaces that drive the individual components of the magnetic resonance tomography apparatus 1 such as the transmitter coil, reception coil or the individual magnets, or in order to receive the image data. For clarity, however, only a common interface 12 for driving the magnetic resonance tomography apparatus 1 and an interface 13 for the reception of image data from the magnetic resonance tomography apparatus 1 are shown.

Alternatively, the entire control device 2 can also be integrated into the nuclear magnetic resonance tomography apparatus 1.

In addition to the aforementioned interfaces 12, 13, the computer 7 of the control device includes a processor 9, for example a CPU with adequate computing power, a bulk storage 10, an interface 11 for connection to the terminal 3 as well as a further interface 14 for connection to a measuring instrument, for example an EKG measuring device 21. All of these components are connected to one another with a bus 8.

The program required for the control of the magnetic resonance tomography apparatus 1 run on the processor 9. The control software required therefor is shown with dashed lines in FIG. 1 as a control software module 15. The control software module 15 contains corresponding sub-modules 16, 17, 18, 19, 20 in order to implement the inventive method.

In addition to the illustrated components, of course, the computer 7 also includes all other hardware components that are usually present in such a computer 7, for example an adequate RAM memory, an exchangeable data storage, etc., and the usual software components, for example an operating system, etc. For clarity, these components are not shown, since the exact structure of the computer 7, i.e. the hardware and software architecture, has no significant influence on the invention—unless stated otherwise. It should be noted that the parts of the user interface such as the picture screen 6, the keyboard 4 or the mouse 5 also can be directly connected to the computer 7 instead of employing a separate terminal 3. Likewise, the terminal 3 can assume tasks of the control software module 15 as, for example, a workstation. For example, the terminal 3 can have its own image memory for storing reference images or the like.

For planning a measurement, reference images R on which the subject O is reproduced are presented on the graphic user interface B of the terminal 3. The positions of tomograms to be subsequently acquired are then defined within these reference images R in the form of slice position markings M—section lines through the subject O in this case—with the assistance of the mouse 5 and/or the keyboard 4. The position data of the slice position markings M within the reference images R are forwarded via the interface 11 and the bus 8 to the control software 15 on the processor 9.

The positions of the desired tomograms in subject O itself that correspond to the slice position markings M are calculated in a slice position determination module, referred to below as GSP module 16. Via the bus 8 and the control interface 12, the control software module 15 then controls the individual components of the magnetic resonance tomograph 1 such that the tomograms are acquired at the desired positions. The data of the acquired tomograms are re-supplied to the computer 7 via the interface 13 and stored in the bulk memory 10 and/or are directly presented on the picture screen 6 of the terminal 3. By means of appropriate inputs via the keyboard 4 or with the mouse 5 within the graphic user interface B, for example by means of inputs in a menu shown thereat, the operator always has the possibility of fetching arbitrary tomograms from the bulk storage 10 and having them presented on the picture screen 6.

In order to be able to output the tomograms in durable form at any time, for example on paper or in the form of negatives on a film, etc., a suitable output device such as, for example, a printer is connected to the control device 2. This device and the appertaining interface for the connection to the bus 8, however, are not shown in FIG. 1.

In the inventive exemplary embodiment according to FIG. 1, the control software module 15 includes an image sequence generating module 18, i.e. a further sub-routine, that—following the instructions of the operator via the terminal 3—generates a sequence of time-dependent reference images $R_1$ through $R_6$. Relative acquisition time are respectively allocated to these reference images $R_1$ through $R_6$ when generated.

Figure 2:
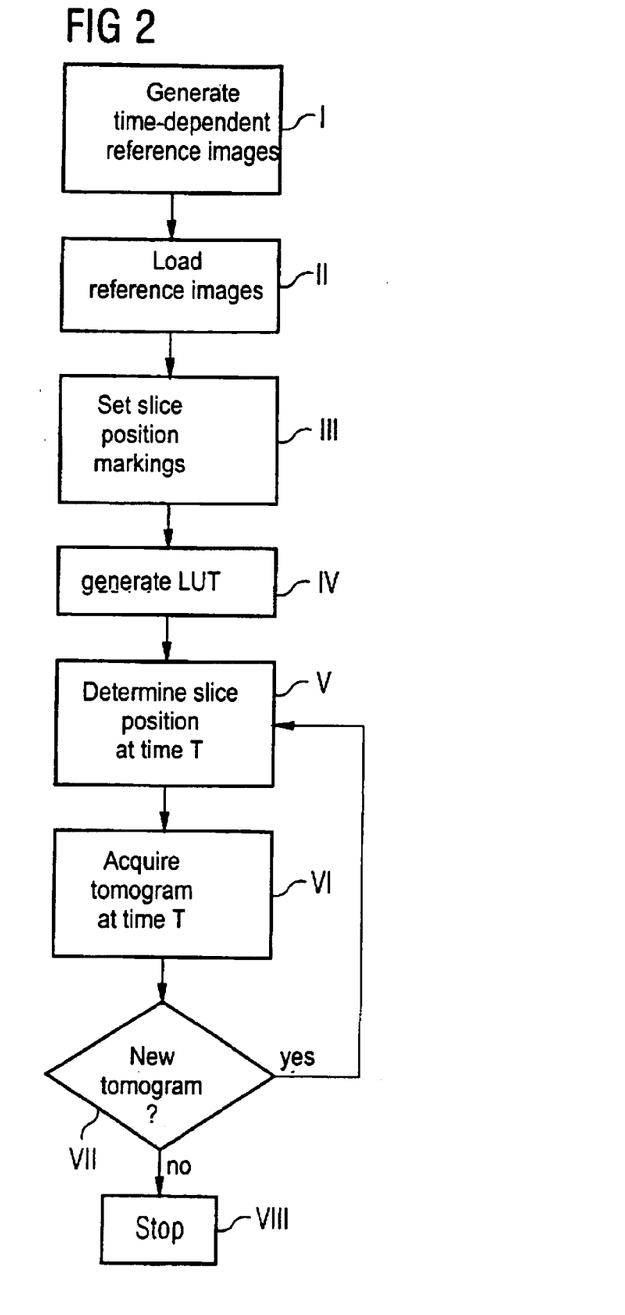
FIG. 2 is a flowchart of an exemplary procedure for planning and implementation of an examination according to the inventive method.

This is shown as the first method step I in the flowchart according to FIG. 2. In a further method step II, the time-dependent reference images $R_1$ through $R_6$ are then loaded into the GSP module 16 and/or into the bulk storage 10. A reference image store RBS is located in the bulk storage 10 in order to store the series of reference images $R_1$ through $R_6$ and which allows them to be to recalled therefrom at any time. The GSP module 16 then sees to it that the time-dependent reference images $R_1$ through $R_6$ to be presented on the user interface B of the terminal 3 either automatically or when called by the operator.

Figure 3:
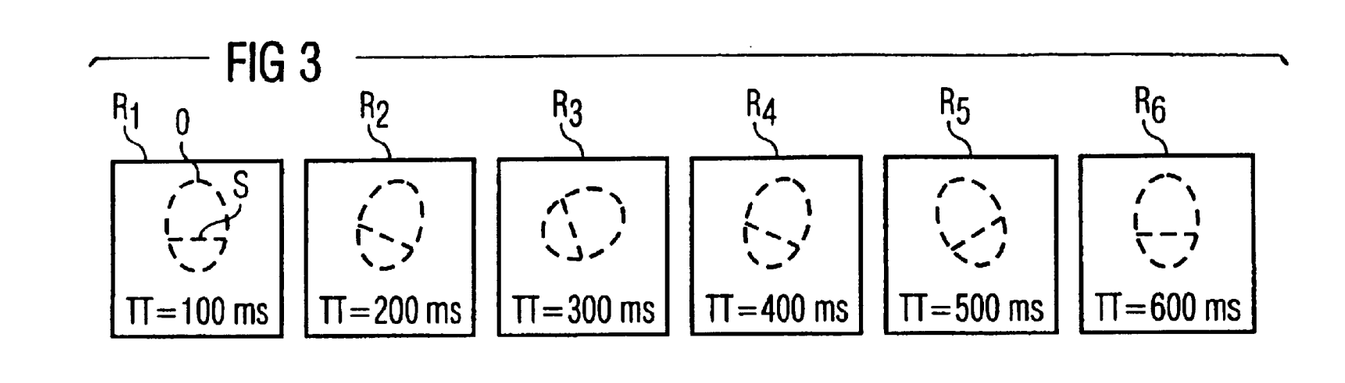
FIG. 3 is a schematic illustration of a sequence of time-dependent reference images.

Such a series of six time-dependent reference images $R_1$ through $R_6$ is shown in FIG. 3. The subject O shown on the reference images $R_1$ through $R_6$ is schematically shown by means of a broken line ellipsoid. A structure S is located within the subject O, the structure S being indicated as a cross-bar within the lower third of the ellipsoid, for simplicity. Each of these reference images $R_1$ through $R_6$ was acquired at a different acquisition time that is indicated within the reference image $R_1$ through $R_6$. The first reference image $R_1$, thus, was acquired 100 ms after a reference time, the second reference image $R_2$ 200 ms after the reference time, etc.

Within method step III according to FIG. 2, respective slice position markings $M_1$ through $M_6$ are set in the reference images $R_1$ through $R_6$. This is accomplished by the operator entering section lines of projection presentations within the illustrated reference images $R_1$ through $R_6$ in the usual way with the keyboard 4 and/or the mouse 5.

Figure 4:
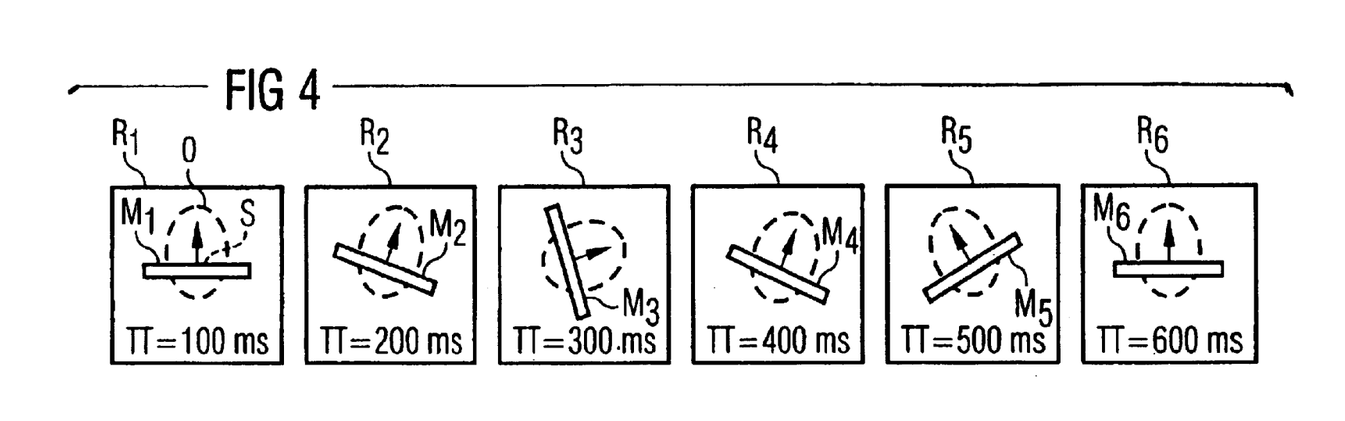
FIG. 4 is an illustration of the sequence of reference images according to FIG. 3, each with schematically entered slice position markings.

This is schematically shown in FIG. 4 for the reference images $R_1$ through $R_6$ shown in FIG. 3. The individual slice position markings $M_1$ through $M_6$ are shown as broad bars that respectively cover the structure S of interest of the subject O in the individual reference images $R_1$ through $R_6$. A tomogram that shows exactly this structure S thus is subsequently acquired later.

The relative acquisition time of each reference image $R_1$ through $R_6$ is automatically allocated as a time mark TT to the individual slice position markings $M_1$ through $M_6$. This occurs in an allocation device 19, which is a sub-routine of the GSP module 15 here.

The data of the slice position markings M1 through M6 with the appertaining time mark TT are then further-processed in the GSP module 16. To this end, the GSP module 16 includes a further software module 20 that generates a look-up table LUT from the given slice position markings M1 through M6 with the appertaining time marks TT, the look-up table LUT, for example, being able to be stored in the bulk storage 10. For example, such a look-up table LUT can have the following arrangement:

| Time TT in ms | Origin position (LPH) | Slice normal (LPH) | In-plane vector (LPH) |
| --- | --- | --- | --- |
| 100 | p[l, p, h] (1) | n[l, p, h] (1) | v[l, p, h] (1) |
| 200 | p[l, p, h] (2) | n[l, p, h] (2) | v[l, p, h] (2) |
| 300 | p[l, p, h] (3) | n[l, p, h] (3) | v[l, p, h] (3) |
| 400 | p[l, p, h] (4) | n[l, p, h] (4) | v[l, p, h] (4) |
| 500 | p[l, p, h] (5) | n[l, p, h] (5) | v[l, p, h] (5) |
| 600 | p[l, p, h] (6) | n[l, p, h] (6) | v[l, p, h] (6) |

In this exemplary embodiment, the time mark TT that indicates the relative point in time is entered in the first column. The other three columns respectively indicate the position data p, n, v that are needed in order to unambiguously define the position of the respective tomogram.

In the illustrated exemplary embodiment, these are the coordinates of a defined origin p in the second column, for example the geometrical mid-point or a defined corner of a tomogram.

The coordinates of the slice normal n, i.e. of the vector that projects out of the slice plane, are recited in the third column. In the reference images $R_1$ through $R_6$ in FIG. 4, the slice normal vector is entered as an arrow residing perpendicular to the slice position marking $M_1$ through $M_6$; the origin is the respective intersection of the arrow with the slice position marking $M_1$ through $M_6$.

The origin and the slice normal vector are the parameters that are needed in order to define the position of a planar, plane-parallel, two-dimensional tomogram.

Added thereto as a third parameter in the illustrated look-up table is the in-plane vector v that characterizes the edge orientation of the tomogram. This is the vector that defines the direction of the first line of an acquired, two-dimensional tomogram. This in-plane vector is an optional parameter that alternatively could be kept constant, however, the employment of the in-plane vector v is meaningful when the structure under observation moves not only transversely relative to the tomogram plane but also executes rotational movements in the tomogram plane. These rotational movements can be compensated by means of a variation of the in-plane vector v with time.

If more complicated tomograms, for example hyperbolic planes or tomograms differing in thickness, are to be acquired, appropriately further parameters must be defined and entered into the look-up table, or be taken into consideration in the determination of the positioning function.

The individual parameters are respectively indicated in the illustrated look-up table in a coordinate system (LPH) defined by the position of the patient. The first coordinate L (left) is the direction to the left side of the patient; the second coordinate P (posterior) is the direction to the back of the patient; and the third coordinate H (head) proceeds in head direction of the patient. The origin of the coordinate system relative to the anatomy of the patient is determined by the measurement. The origin is usually the mid-point of the nuclear magnetic resonance tomography apparatus 1 since the magnetic field is very homogeneous in that region. The patient is therefore positioned such that the region to be measured lies in the proximity of the midpoint of the magnetic resonance tomography apparatus 1. As a rule, the origin thus also lies in the proximity of the structure to be examined, for example directly at the heart in the case of heart measurements.

In the following measurements, the look-up table LUT is used so as to employ the position data of tomograms stored therein as supporting points dependent on time, and thus to determine a particular, exact position at an arbitrary time by interpolation between the values in the look-up table LUT. This occurs in a slice calculation unit 17, which is again a sub-routine of the GSP module 15 in the exemplary embodiment.

In the flowchart according to FIG. 2, the actual, subsequent measurement begins with method step V. The exact slice position for an acquisition time T is determined with the assistance of the reference table LUT. Subsequently, the tomogram is acquired exactly at the acquisition time T.

In a further method step VII, a decision is made as to whether a new tomogram is to be acquired. If so, then the new calculation of the slice position for the new time T in turn ensues in method step V, etc. When all desired tomograms have been acquired, then the measurement is stopped in method step VIII.

Figure 5:
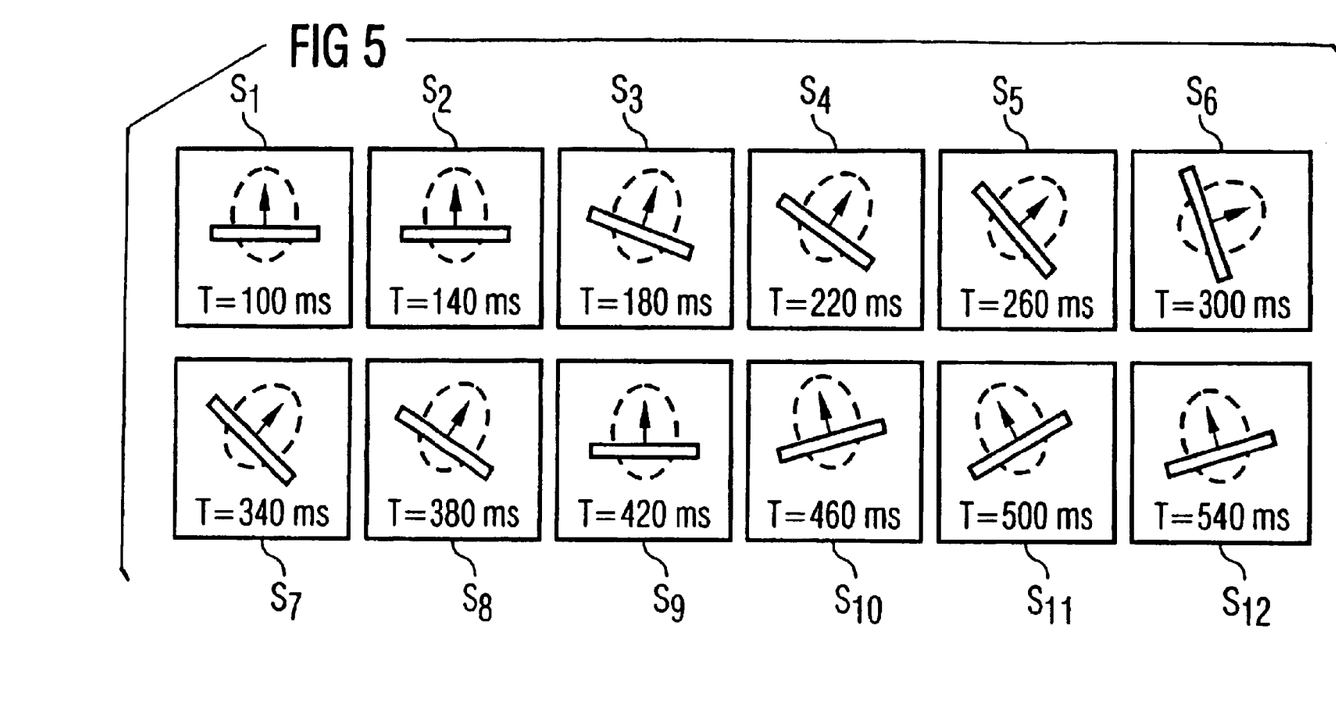
FIG. 5 is a schematic illustration of the position of the subject to be measured and of the position of the tomogram to be acquired in a series of twelve individual tomograms at different relative points in time.

An example of an acquired measurement series is schematically shown in Figure V. A total of 12 tomograms $S_1$ through $S_{12}$ have been generated within the measurement series. As in the case of the reference images $R_1$ through $R_6$, the respective acquisition times lie between 100 and 600 ms, however, the acquisition times T need not coincide with the relative acquisition times of the reference images $R_1$ through $R_6$, i.e. with the time marks TT of the individual slice position markings $M_1$ through $M_6$.

Figure 6:
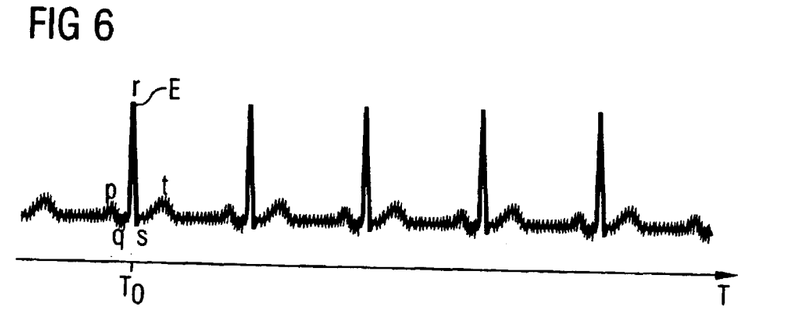
FIG. 6 is an illustration of an EKG for using the r-wave of the EKG as the reference time for a tomogram acquisition.

In order, for example, to select a suitable reference time $T_0$ for an examination of the heart valve, the patient's EKG is continuously obtained during the examination and an event within this EKG is employed as a trigger signal for determining the reference time $T_0$. This is shown in FIG. 6. The EKG exhibits the typical p-q-r-s-t waveform. The easily discernable rise of the r-wave is available as event E both to trigger the measurement for producing the series of reference images $R_1$ through $R_6$ as well as, later, the actual measurement. In the exemplary embodiment shown in FIG. 1, the control device includes an EKG device 21 that is connected to the computer 7 via the interface 21. This EKG device 21 registers the rise of the r-wave and sends a trigger signal TS to the computer 7. This trigger signal TS is then used as start signal for triggering the measurement of the reference images, or in the later subsequent actual examination.

As these exemplary embodiments show, the invention offers the user the possibility of interactively defining an arbitrary slice position as a function of time. No additional measurements are fundamentally required. This method can nonetheless be linked at any time to automatic methods for determining slice positions. For example, supporting points can be automatically calculated in advance with a known, standard slice tracking method and can be offered on the user interface within the graphic positioning in order to speed up the method when planning an examination. The operator then always has the possibility of accepting these offered slice position markings or of arbitrarily modifying or deleting them.

The method also has the advantage that the presentation of the motion of the structure under examination can be implemented with significantly higher spatial resolution and in a number of orientations. It therefore allows a more exact positioning than other methods.

Further, a method for prescribing a time-dependent slice position in three dimensions is available that is independent of algorithms and other methods. Additionally, the method has the advantage that the actual measurement during the examination is freed of the need for additional registration of the position dependent on the time. The actual measurement therefore can ensue faster.

The method can be employed especially well in an acquisition of periodic motions. In particular, and in contrast to other methods, it is also possible to define a slice dislocation that is independent of periodic motions.

The prescription of the slice positioning is not limited to two-dimensional planes but—as mentioned above—can be expanded to the prescription of three-dimensional volumes and hyperbolic surfaces. Although the invention has been primarily explained with reference to medical examples, it is not limited to such a use.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for controlling a tomogram acquisition device for acquiring tomograms of a subject, comprising the steps of:
   presenting a plurality of reference images of a subject at a graphic user interface;
   setting a sequence of time-dependent slice position markings respectively in the reference images with a time mark allocated to each of said slice position markings in said sequence; and
   dependent on said sequence, determining respective positions of tomograms to be acquired from said subject by designating respective acquisition times for the tomograms relative to a reference time.

2. A method as claimed in claim 1 comprising generating said reference images in a reference image sequence showing said subject at respectively different relative points in time, and setting said sequence of time-dependent slice position markings in said reference image sequence.

3. A method as claimed in claim 2 comprising setting the respective slice position markings in said reference images, as said time mark, as a same relative point in time as the relative point in time of the respective reference image.

4. A method as claimed in claim 2 comprising setting one and only one slice position marking in each of said reference images.

5. A method as claimed in claim 4 comprising generating said sequence of reference images to show a specified structure of said subject in respectively different positions, and wherein the slice position markings in the respective reference images designate a slice of said subject comprising said structure.

6. A method as claimed in claim 1 comprising generating a time-dependent positioning function from said sequence of time-dependent slice position markings and storing said positioning function and using said function at a subsequent measuring time for obtaining said tomograms at said respective positions.

7. A method as claimed in claim 1 comprising generating a time-dependent look-up table from said sequence of time-dependent slice position markings and storing said look-up table and using said function at a subsequent measuring time for obtaining said tomograms at said respective positions.

8. A method as claimed in claim 1 comprising employing, as said reference time, a starting time of an exposure series in which said tomograms are acquired.

9. A method as claimed in claim 1 comprising employing, as said reference time, a time of occurrence of a specified event associated with said subject.

10. A method as claimed in claim 8 comprising employing a periodically re-occurring event as said specified event.

11. A method as claimed in claim 9 comprising acquiring said time of occurrence of said specified event with a measuring instrument interacting with said subject.

12. A method as claimed in claim 11 comprising generating a trigger signal at said point of time of occurrence of said specified event for triggering a start of an exposure series in which said tomograms are acquired.

13. A control device for controlling a tomogram acquisition device for acquiring tomograms of a subject, comprising:
   a graphic user interface for presenting a plurality of reference images of a subject at a graphic user interface and for setting a sequence of time-dependent slice position markings respectively in the reference images with a time mark allocated to each of said slice position markings in said sequence;

a slice position determination unit for, dependent on said sequence, determining respective positions of tomograms to be acquired from said subject by designating respective acquisition times for the tomograms relative to a reference time; and a control unit for operating a tomogram acquisition device to acquire said tomograms at said respective positions.

14. A control device as claimed in claim 13 wherein said graphic user interface presents said reference images in a reference image sequence showing said subject at respectively different relative points in time, and sets said sequence of time-dependent slice position markings in said reference image sequence.

15. A control device as claimed in claim 14 wherein said graphic user interface sets the respective slice position markings in said reference images, as said time mark, at a same relative point in time as the relative point in time of the respective reference image.

16. A control device as claimed in claim 15 wherein said graphic user interface sets one and only one slice position marking in each of said reference images.

17. A control device as claimed in claim 16 wherein said graphic user interface presents said sequence of reference images to show a specified structure of said subject in respectively different positions, and wherein the slice position markings in the respective reference images designate a slice of said subject comprising said structure.

18. A control device as claimed in claim 13 wherein said slice position determination unit generates a time-dependent positioning function from said sequence of time-dependent slice position markings and comprises a memory accessible by said control unit for storing said positioning function, and wherein said control unit uses said function at a subsequent measuring time for obtaining said tomograms at said respective positions.

19. A control device as claimed in claim 13 wherein said slice position determination unit generates a time-dependent look-up table from said sequence of time-dependent slice position markings and comprises a memory accessible by said control unit for storing said look-up table, and wherein said control unit said uses said function at a subsequent measuring time for obtaining said tomograms at said respective positions.

20. A control device as claimed in claim 13 wherein said slice position determination unit employs, as said reference time, a starting time of an exposure series in which said tomograms are acquired.

21. A control device as claimed in claim 13 wherein said slice position determination unit employs, as said reference time, a time of occurrence of a specified event associated with said subject.

22. A control device as claimed in claim 20 wherein said slice position determination unit employs a periodically re-occurring event as said specified event.

23. A control device as claimed in claim 21 comprising a measuring instrument adapted to interact with said subject for acquiring said time of occurrence of said specified event.

24. A control device as claimed in claim 23 wherein said control unit generates a trigger signal at said point of time of occurrence of said specified event for triggering a start of an exposure series in which said tomograms are acquired.

25. A tomogram acquisition device comprising:

a graphic use interface for presenting a plurality of reference images of a subject at a graphic user interface and for setting a sequence of time-dependent slice position markings respectively in the reference images with a time mark allocated to each of said slice position markings in said sequence;

a slice position determination unit for, dependent on said sequence, determining respective positions of tomograms to be acquired from said subject by designating respective acquisition times for the tomograms relative to a reference time;

a tomogram acquisition unit adapted to interact with said subject to acquire tomograms from said subject; and a control unit for operating said tomogram acquisition unit to acquire said tomograms at said respective positions.

* * * * *